United States Patent [19]

Rugland et al.

[11] Patent Number: 5,584,874
[45] Date of Patent: Dec. 17, 1996

[54] MEDICAL ELECTRICAL LEAD HAVING IMPROVED ANCHORING SLEEVE

[75] Inventors: Roger E. Rugland, Anoka; Norbert H. Cannon, Shoreview, both of Minn.; Harlen Daman, Alamo, Tex.

[73] Assignee: Medtronic, Inc., Minneapolis, Minn.

[21] Appl. No.: 430,962

[22] Filed: Apr. 28, 1995

[51] Int. Cl.⁶ .................................................... A61N 1/05
[52] U.S. Cl. .................................................... 607/132
[58] Field of Search .................................... 607/126, 129, 607/132

[56] References Cited

U.S. PATENT DOCUMENTS

| | | |
|---|---|---|
| 3,176,690 | 5/1965 | H'Doubler . |
| 3,730,187 | 5/1973 | Reynolds . |
| 3,788,328 | 1/1974 | Alley et al. . |
| 3,821,957 | 7/1974 | Riely et al. . |
| 3,880,169 | 4/1975 | Starr et al. . |
| 4,114,626 | 9/1978 | Beran . |
| 4,122,858 | 10/1978 | Schiff . |
| 4,230,110 | 10/1980 | Beroff . |
| 4,235,232 | 11/1980 | Spaven . |
| 4,266,552 | 5/1981 | Dutcher . |
| 4,276,882 | 7/1981 | Dickhudt et al. . |
| 4,278,092 | 7/1981 | Borsanyi et al. . |
| 4,287,891 | 9/1981 | Peters . |
| 4,332,259 | 7/1982 | McCorkle, Jr. . |
| 4,411,654 | 10/1983 | Boarini et al. . |
| 4,419,819 | 12/1983 | Dickhudt et al. . |
| 4,437,475 | 3/1984 | White . |
| 4,516,584 | 5/1985 | Garcia . |
| 4,553,961 | 11/1985 | Pohndorf et al. . |
| 4,597,756 | 7/1986 | Raible . |
| 4,672,979 | 6/1987 | Pohndorf . |
| 4,683,895 | 8/1987 | Pohndorf . |
| 4,860,750 | 8/1989 | Frey . |
| 5,036,862 | 8/1991 | Pohndorf . |
| 5,107,856 | 4/1992 | Kristiansen et al. . |
| 5,129,405 | 7/1992 | Milijasevic et al. . |
| 5,152,298 | 10/1992 | Kreyenhagen et al. . |
| 5,242,431 | 9/1993 | Kristiansen . |
| 5,273,053 | 12/1993 | Pohndorf . |
| 5,376,108 | 12/1994 | Collins et al. . |
| 5,423,763 | 6/1995 | Helland et al. . |

FOREIGN PATENT DOCUMENTS

| | | |
|---|---|---|
| 0625359 | 5/1994 | European Pat. Off. . |
| 2662310 | 11/1991 | France . |

*Primary Examiner*—William E. Kamm
*Assistant Examiner*—Scott M. Getzow
*Attorney, Agent, or Firm*—Michael J. Jaro; Harold R. Patton

[57] ABSTRACT

A medical electrical lead which features an improved anchoring sleeve. Specifically the anchoring sleeve has a first end and a second end and further has a series of circumferential suture grooves thereabout. A longitudinally extending slot is provided across each circumferential suture groove. Each slot extends across each groove but is separate from every other slot. In such a manner the area of the anchoring sleeve may be compressed in the area of the groove due to the relevant slot. Because each slot, however, only extends across one groove, the lead body is not otherwise easily compressed in the area away from each groove. Thus the sleeve does not unintentionally engage with and frictionally interfere with the lead body therethrough unless so intended. In the preferred embodiment the anchoring sleeve has three circumferential grooves, each groove having a slot through the anchor sleeve which extends across.

2 Claims, 4 Drawing Sheets

MEDICAL ELECTRICAL LEAD HAVING IMPROVED ANCHORING SLEEVE

FIELD OF THE INVENTION

This invention relates to the field of body implantable medical electrical leads, and in particular to a body implantable medical electrical lead which features an improved anchoring sleeve.

BACKGROUND OF THE INVENTION

In the medical field, various types of body implantable leads are known and used. One type of commonly used implantable lead is an endocardial pacing lead.

Endocardial pacing leads are attached at their proximal end to an implantable pulse generator and at their distal end to the endocardium of a cardiac chamber. The distal end of an endocardial lead may engage the endocardium by either an active fixation mechanism or a passive fixation mechanism.

Active fixation mechanisms use a structure, such as helix or hook, to physically engage into or actively affix themselves onto the heart. Passive fixation mechanisms, such as a tine assembly, lodge or passively fix themselves to the heart.

A preferred means for introducing an endocardial lead into the heart is through a vein. During the implantation of an transvenous endocardial lead body, the lead may be introduced into the heart using either the subclavian or cephalic vein in the shoulder area under the pectoral muscle.

To anchor the lead body at the venous entry site, the lead body is secured to an anchoring sleeve, the anchoring sleeve, in turn, is secured to the surrounding fascia or tissue. Generally the lead body is secured to an anchoring sleeve through a series of circumferential sutures wrapped around the anchoring sleeve to thereby squeeze or compress the sleeve to the lead. The sleeve itself is additionally secured to the surrounding fascia or tissue through further sutures.

Anchoring sleeves in present use are generally tubular structures molded out of a soft, implantable elastomer such as silicone. Such sleeves may be implanted as follows: First, the anchoring sleeve is slid along the lead body to the location at which the lead is to be anchored to the underlying tissue. One or more sutures are then tied around the sleeve to compress it and thereby secure it to the lead body. Circumferential grooves in the outer surface of the sleeve are typically provided for this purpose. The last step is to anchor the sleeve to adjacent body tissue; sutures may be passed through a pair of tabs projecting from the sleeve to provide the required anchoring.

This type of common design has evolved due to the conflicting performance criteria anchoring sleeves generally have. First, because not all patients are the same size and not all doctors introduce the lead into the vein at exactly the same site relative in distance to the heart, it is necessary for the anchoring sleeve to be able to be slid or moved along the lead body to permit it to be properly located along the lead prior to being secured thereto.

Although anchoring sleeves must be able to be slid along a lead body, they must also be able to be securely attached to the lead body. To date a preferred method of attaching or affixing the sleeve and lead body together is by frictionally engaging the lead body and sleeve. Typical anchoring sleeves are frictionally attached to a lead body through sutures tightly wrapped about the sleeve in conjunction with the use of a material for the sleeve which has a relative high coefficient of friction against the lead body. U.S. Pat. No. 4,553,961 to Pohndorf et al., for example, discloses an anchoring sleeve featuring a gripping enhancing structure to facilitate gripping of the lead body. One drawback to such a design is that the gripping structure may be a second part, thereby complicating manufacturing and increasing cost. A more serious drawback with such a design is that the gripping structure often unintentionally engages and thus locks to the lead body, such as when a physician grasps the anchoring sleeve and simply tries to position it along the lead body.

Because anchoring sleeves typically are difficult to slid along the lead body, they have often been made having a larger diameter central lumen or throughbore (i.e. bore in the sleeve through which the lead body passes) than the lead body. That solution, however, itself created performance difficulties. Namely because the sleeve has a larger inner diameter than the outer diameter of the lead body, it was made difficult to sufficiently compress or squeeze the sleeve so as to grip about the lead body.

In order to permit the sleeve to be sufficiently compressed or squeezed through sutures, sleeves have often featured slots or slits across the sleeve. U.S. Pat. No. 4,516,584 to Garcia, for example, discloses the use of four slits located between the suture grooves. These slits permitted the sleeve to be squeezed by the sutures and thereby securely frictionally engage the lead body.

One drawback to the design of Garcia, however, is that the slits go only between the suture grooves, thereby providing only a limited ability to be squeezed against the lead body. U.S. Pat. No. 5,129,405 to Milijasevic et al. apparently attempted to solve this drawback of Garcia by providing a slit entirely across the length of the sleeve, including completely across the suture grooves. Through such a design, it appears the lead may be squeezed in the area not only between the grooves, but also in the area outside the grooves and across the entire length of the sleeve.

One serious drawback with the design of Milijasevic et al. is that the sleeve may be readily squeezed against the lead body by simple handling. That is, when the physician grasp the sleeve in an effort to properly position it along the lead body, even minor pressure from the doctor's fingertips may cause the sleeve to frictionally engage the lead body, thereby greatly inhibiting its ability to be moved to the proper location.

SUMMARY OF THE INVENTION

It is thus an object of the invention to provide a medical electrical lead which features an improved anchoring sleeve.

It is a further object of the invention to provide an improved anchoring sleeve which will permit the sleeve to be squeezed by sutures and thereby securely frictionally engage the lead body throughout the area of the sutures.

It is a further object of the invention to provide an improved anchoring sleeve which will permit a physician to grasp the sleeve and position the anchoring sleeve along the lead body without causing the sleeve to frictionally engage the lead body due to the pressure from the physician's fingertips.

These and other objects are met by the present invention which concerns a medical electrical lead which features an improved anchoring sleeve. Specifically the lead has a connector assembly, a conductor attached thereto and an electrode electrically coupled to the conductor. An insulative sleeve covers the conductor and an annular anchoring sleeve is movably positioned over the insulative sleeve. The anchoring sleeve has a first end and a second end and further has a series of circumferential suture grooves thereabout. A longitudinally extending slot is provided across each circumferential suture groove. Each slot extends across each groove but is separate from every other slot. In such a manner the area of the anchoring sleeve may be compressed in the area of the groove due to the relevant slot. Because each slot, however, only extends across one groove, the lead body is not otherwise easily compressed in the area away from each groove. Thus the sleeve does not unintentionally engage with and frictionally interfere with the lead body therethrough unless so intended. For example, minor pressure from the doctor's fingertips may cause the sleeve to compress and frictionally engage the lead and thus inhibit its ability to be moved to the proper location. In the preferred embodiment the anchoring sleeve has three circumferential grooves, each groove having a slot through the anchor sleeve which extends across.

The FIGS. are not necessarily to scale.

DESCRIPTION OF THE PREFERRED EMBODIMENT

For the purposes of this specification and claims, the term "lead" is used herein in its broadest sense and includes pacing or defibrillation leads as well as any other types of stimulation leads, a sensing leads, any combination thereof or any other elongated member, such as a catheter or tube, which may usefully be used within the body.

Figure 1:
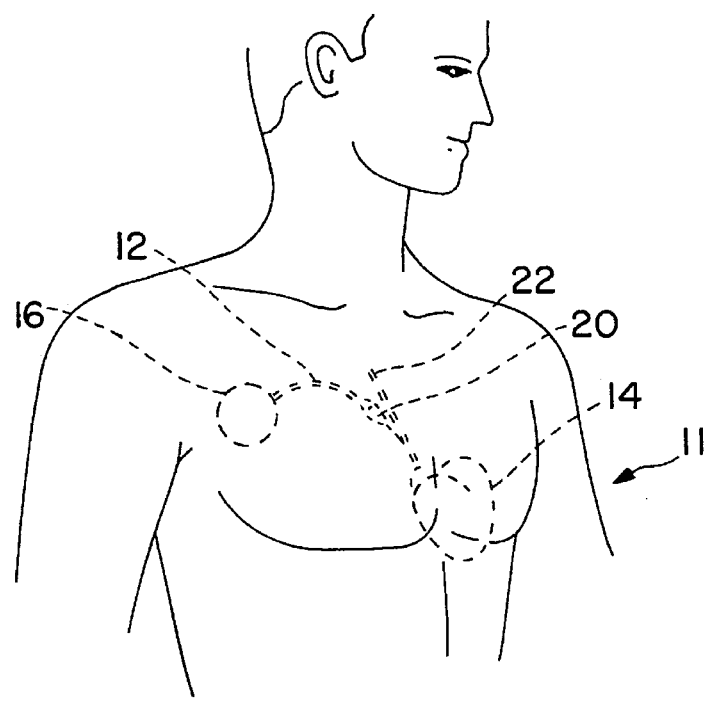
FIG. 1 is a fragmentary view of the chest of a male showing in phantom the position of a pacing lead and pacer implanted in the male's chest.

Referring now to the drawings in greater detail there is illustrated in FIG. 1 the outline of the upper torso or chest of a human male 11 wherein there is shown in phantom a lead 12 extending between heart 14 and pulse generator 8 implanted in a pocket adjacent or under the shoulder of male 11.

Also shown in FIG. 1 is an anchoring sleeve 20 constructed in accordance with the teachings of the present invention and situated on lead 12 as it enters a vein 22.

Figure 2:
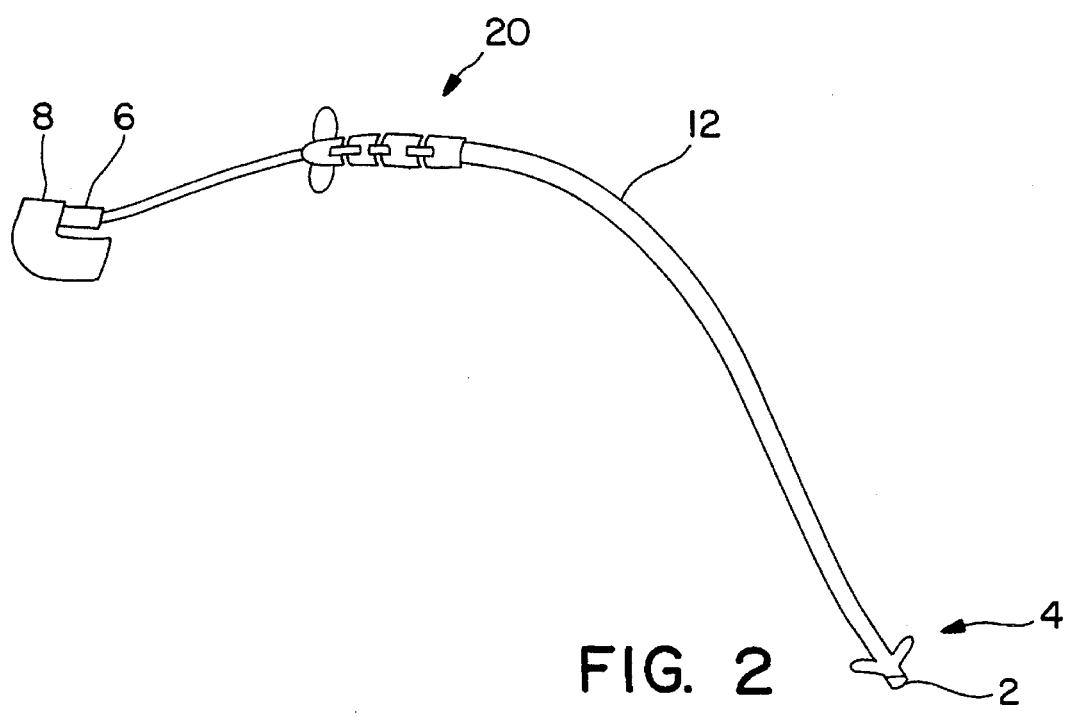
FIG. 2 is a perspective view of a pacing system featuring the improved anchoring sleeve.
Figure 3:
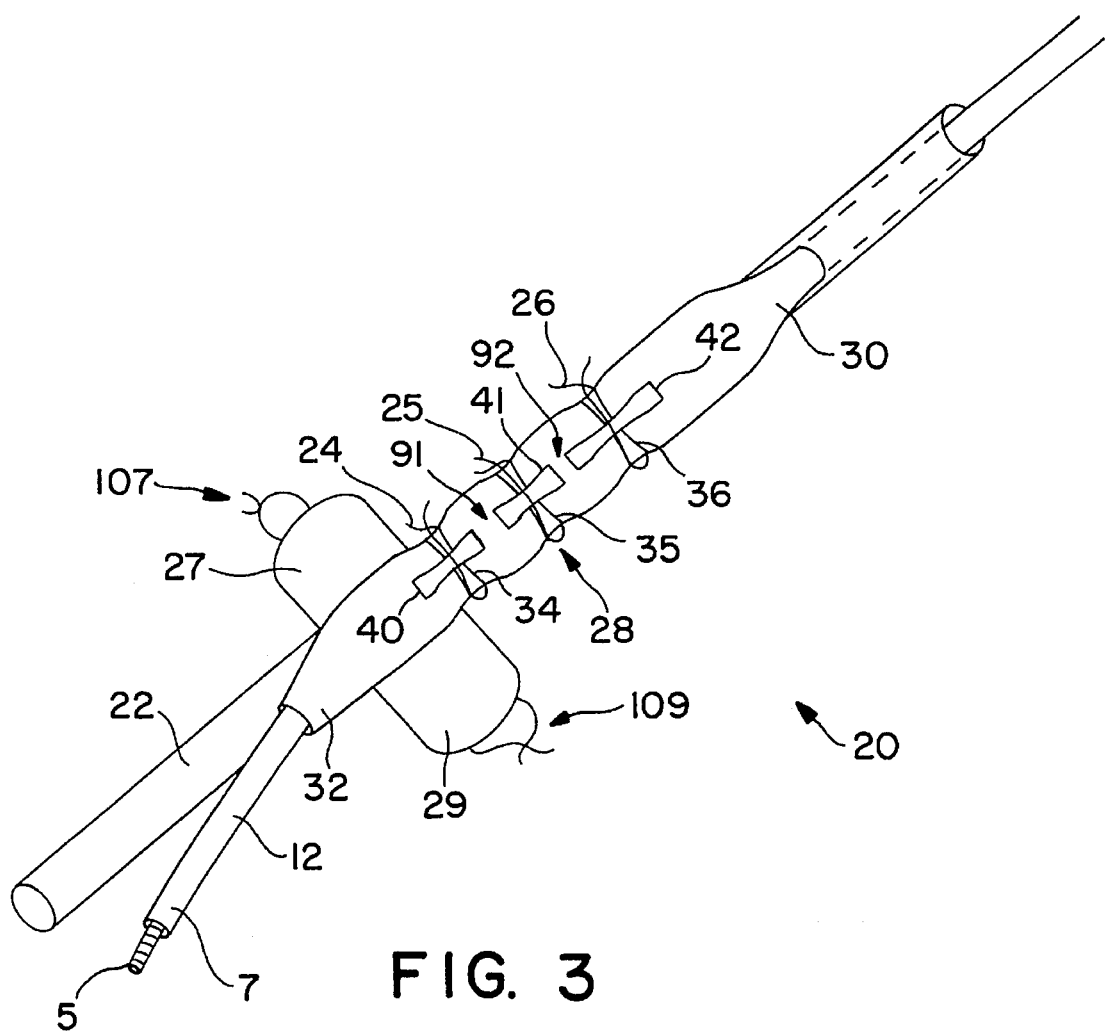
FIG. 3 is a detailed perspective view of the improved anchoring sleeve of the present invention surrounding a lead body of a pacing lead at its entry point into a vein.

FIG. 2 is a perspective view of a pacing system featuring anchoring sleeve 20. As seen, anchoring sleeve 20 is positioned about lead 12. Lead 12 feature electrode 2 on distal end and tine assembly 4 near distal end. It should be understood other configuration of electrode and fixation devices may be featured on a lead 12 for use in the present invention, including ring electrodes as well as screw-in type leads. The electrode 2 on distal end and tine assembly 4 near distal end are illustrated in FIG. 2 only as an example of one type of lead upon which the improved anchoring sleeve may be used. Connector assembly 6 is positioned at proximal end of lead. Connector assembly 6 electrically couples into pulse generator 8 and may be constructed in any acceptable manner. Such a system delivers electrical pulse from pulse generator 8 through lead 12 to electrode 2. As mentioned above electrode 2 is typically positioned in heart, such as the atrium or ventricle (not shown in this FIG.) Lead 12 may be constructed in any acceptable manner, such as with a coiled conductor 5 insulated by insulative sleeve 7 (as best seen in FIG. 3), all of a type well known in the art. In the preferred embodiment conductor 5 is constructed from multi-filar coils of MP35N and insulative sleeve 7 is made of silicone.

FIG. 3 is a detailed perspective view of anchoring sleeve 20 of the present invention surrounding a lead body of a pacing lead at its entry point into a vein. As seen anchoring sleeve 20 is sutured by sutures 24, 25 and 26 to lead 12. Anchoring sleeve 20 is further sutured to the underlying tissue or fascia (not shown) through tabs 27, 29 and sutures 107 and 109.

Anchoring sleeve 20 is generally cylindrical in shape and has a central portion 28 having circumferential grooves 34, 35 and 36 in anchoring sleeve 20 in which are received sutures 24, 25 and 26 respectively. At the respective ends of central portion 28 are tapering end portions 30 and 32.

Figure 4:
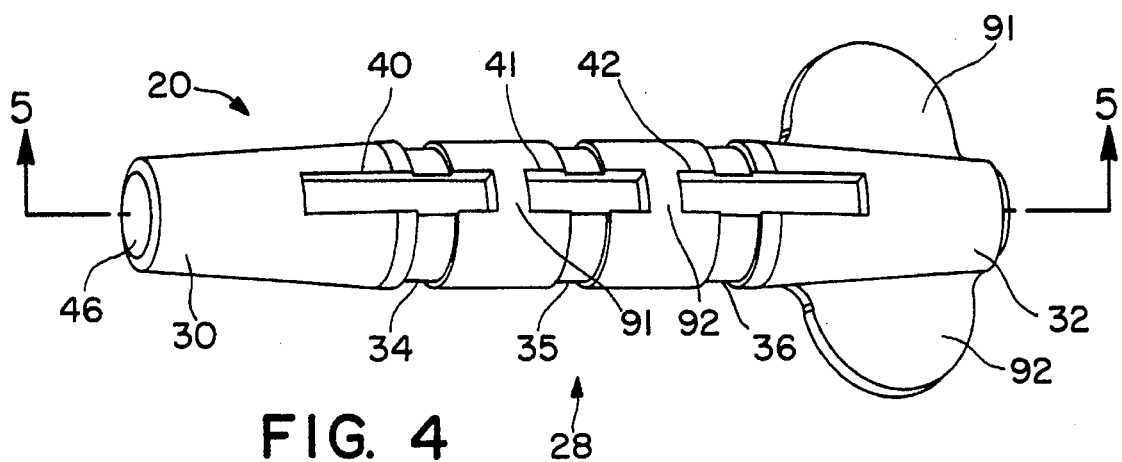
FIG. 4 is a perspective view of the improved anchoring sleeve of the present invention.
Figure 5:
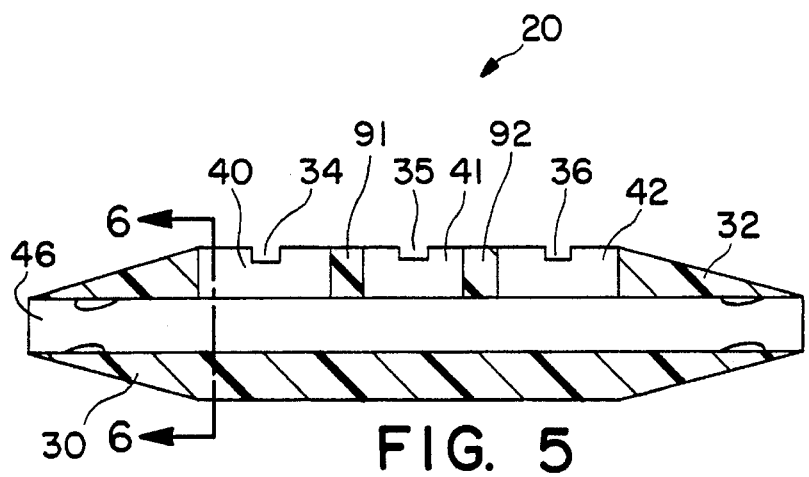
FIG. 5 is a cross-sectional side view of the improved anchoring sleeve of the present invention.
Figure 6:
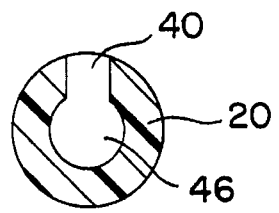
FIG. 6 is a cross-sectional view of the improved anchoring sleeve shown in FIG. 5 taken along the line 6—6.

Central portion 28 has three slots 40, 41 and 42 which extend radially inwardly from the outer cylindrical surface of central portion 28 to throughbore 46 as seen best in FIGS. 4–6. Slots 40, 41 and 42 extend through anchoring sleeve 20 in the area across each respective circumferential grooves 34, 35 and 36. In the preferred embodiment each slot extends longitudinally along anchoring sleeve 20 and perpendicularly across each respective slot, although if desired each slot may be oriented in whatever manner desired in relative to anchoring sleeve 20 and the respective groove. For example, each slot may be canted or non-perpendicular to each groove, or could also be helically oriented along lead 20, if desired. Any geometric orientation of slot to groove and lead 20 which is acceptable may be used. As can be appreciated from FIG. 3, slots 40, 41 and 42 permit anchoring sleeve 20 to be compressed by each suture 24, 25 and 26 proximate to each respective groove 34, 35 and 36 so as to permit anchoring sleeve 20 to grip lead disposed through throughbore 46. In this way, anchoring sleeve 20 is tightly fixed onto lead 12 so that it is prevented from axial or longitudinal movement on lead 12 at its point of entry into vein 22.

Slots 40, 41 and 42 are relatively broad so as to permit anchoring sleeve 20 to be compressed as much as desired by sutures. Each slot, however, is provided to correspond to only one groove, i.e. slot 40 extends only across grove 34. In this fashion anchoring sleeve does not readily collapse as it is handle such that anchoring sleeve engages upon and sticks to the lead therethrough. In other words, the presence of supporting members 91 and 92 between slots 40, 41 and 42 promotes the ability of anchoring sleeve 20 to be readily moved along a lead therethrough without unnecessarily or unintentionally griping, or getting hung upon lead. In such a manner anchoring sleeve 20 permits a physician to grasp anchoring sleeve 20 and position it along lead 12 without causing anchoring sleeve 20 to frictionally engage lead 12 merely due to the pressure from the physician's fingertips.

Anchoring sleeve 20 is preferably made of a silicone elastomer material.

In use, and with reference to FIGS. 1, 2 and 3, an electrode tip (not shown) at the distal end of pacing lead 12 is inserted into vein 22 and then into heart 14. After the electrode tip has been suitable located in a ventricle or atrium of heart 14 and the electrode tip fixed in place therein, anchoring sleeve 20 is moved along lead 12 to the point of entry of lead 12 into vein 22. Then, one or any combination of sutures 24, 25, 26 are tied tightly around anchoring sleeve 20 in grooves 30, 31 and 32 thereby to compress and squeeze sleeve 20 against lead 12 and thus secure sleeve 20 thereto.

Figure 7:
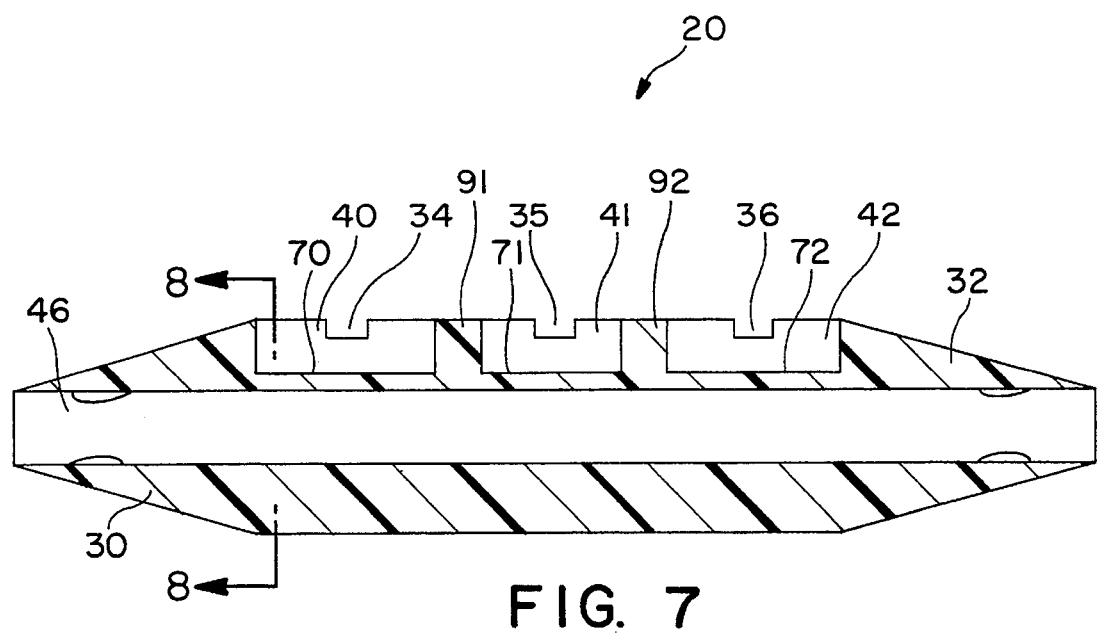
FIG. 7 is a cross-sectional side view of an alternate embodiment of anchoring sleeve of the present invention in which the slot does not extend completely through the wall of sleeve.
Figure 8:
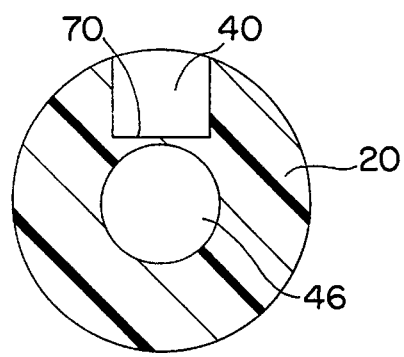
FIG. 8 is a cross-sectional view of the alternate embodiment of anchoring sleeve shown in FIG. 7 taken along the line 8—8.

An alternate embodiment of the improved anchoring sleeve 20 is shown in FIGS. 7 and 8. FIG. 7 is a cross-sectional side view of an alternate embodiment of anchoring sleeve of the present invention in which the slot does not extend completely through the wall of sleeve. As seen, this embodiment is substantially the same as that shown in FIG. 5 (also depicted in FIGS. 2–4) but for the fact that in this embodiment slots 40, 41 or 42 do not extend completely through sleeve 20 from the outer surface to throughbore 46, but rather each slot extends only into sleeve 20 from the outer surface to bottom members 70, 71 and 72 respectively.

FIG. 8 is a cross-sectional view of the alternate embodiment of anchoring sleeve shown in FIG. 7 taken along the line 8—8. As seen in this view, slot 40 only extends from outer surface of sleeve 20 to bottom member 70 (only slot 40 and bottom member 70 are shown in this view for clarity, although slots 41 and 42 and bottom members 71 and 72 respectively are likewise configured.) In the preferred embodiment each bottom member has a thickness of three one-thousandths of an inch (0.003 inches.)

From the foregoing description it will be apparent that the anchoring sleeve of the present invention has a number of advantages, some of which have been described above and others of which are inherent in the invention. Also it will be apparent that modifications can be made to the anchoring sleeve 20 of the present invention without departing from the teachings of the present invention. Thus it should be understood variations and modifications can be effected within the scope of the following claims. Such modifications may include substituting elements or components which perform substantially the same function in substantially the same way to achieve substantially the same result for those described herein.

What is claimed is:

1. A pacing system comprising:

an implantable pulse generator;

a lead, the lead having a conductor and an insulative sleeve, the conductor having a proximal end and a distal end, the proximal end coupled to the pulse generator, the distal end having an electrode, the insulative sleeve insulating the conductor between the proximal end and the distal end; and an anchoring sleeve disposed around the insulative sleeve, the anchoring sleeve having a first end and a second end and further having a series of circumferential suture grooves thereabout, the anchoring sleeve having a longitudinally extending slot across each circumferential suture groove, wherein each slot extends across each groove but is separate from every other slot, each slot extending from an outer surface of the sleeve to an inner surface of the sleeve.

2. The pacing system according to claim 1 wherein said anchoring sleeve is made of silicone.

\* \* \* \* \*